Figure 1:
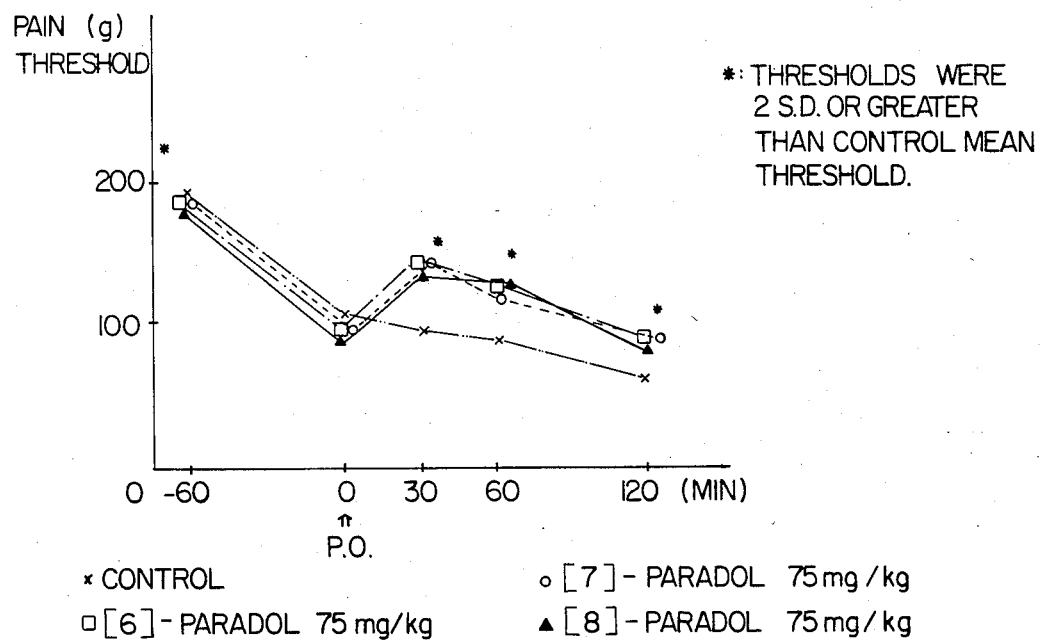

United States Patent [19]
Lee

[11] Patent Number: 4,623,665
[45] Date of Patent: Nov. 18, 1986

[54] METHOD OF PRODUCING ANALGESIA

[76] Inventor: Sang S. Lee, Banpo Apt. 105-502, Banpo-dong, Dongjak-ku, Seoul, Rep. of Korea

[21] Appl. No.: 765,248

[22] Filed: Aug. 13, 1985

[51] Int. Cl.[4] ............................................. A61K 31/12
[52] U.S. Cl. ..................................................... 514/678
[58] Field of Search ......................................... 514/678

[56] References Cited
PUBLICATIONS

Proceedings of the Fifth Asian Symposium on Medicinal Plants and Spices–"Metabolism and Analgesic Effect of Capsaicinoids and Shogaol", Sang Sup Lee, Aug. 20, 1984, pp. 637–646.

Primary Examiner—Stanley J. Friedman
Attorney, Agent, or Firm—Holman & Stern

[57] ABSTRACT

[n]-paradols (n stands for 6, 7 or 8) are useful and powerful analgesics.

8 Claims, 4 Drawing Figures

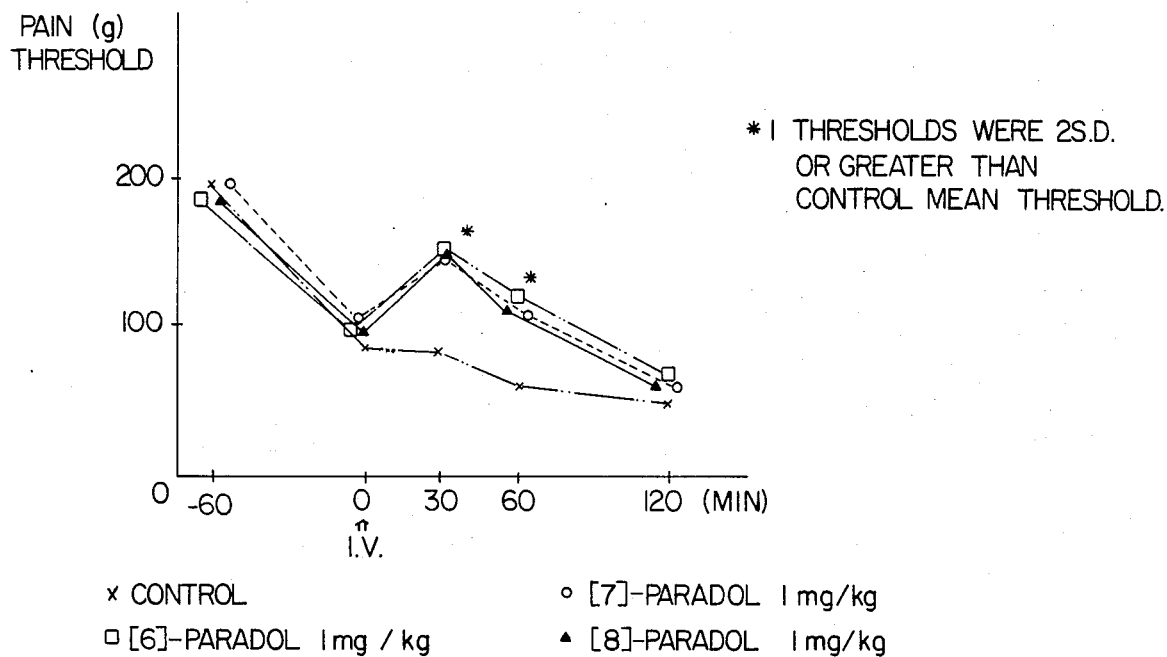
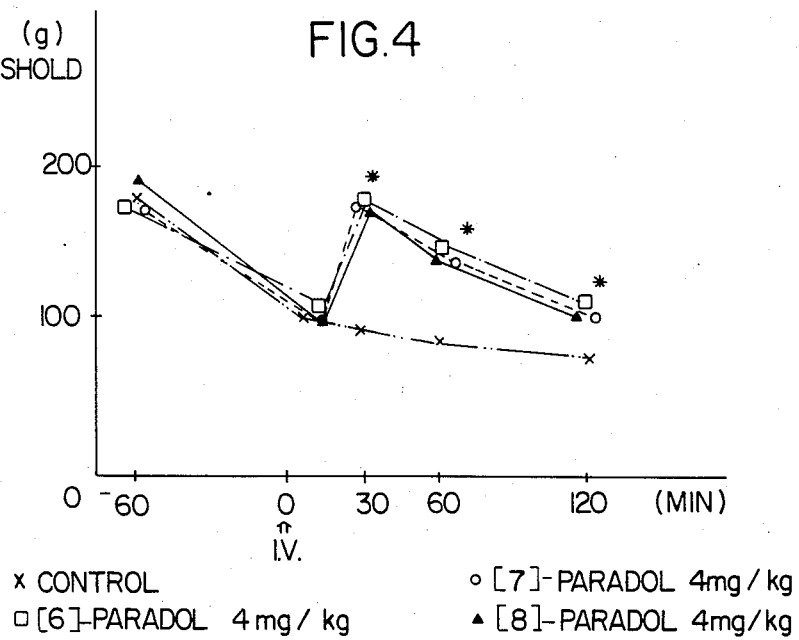

METHOD OF PRODUCING ANALGESIA

This invention relates to the use of [n]-paradols to produce analgesia.

In general, analgesics fall into two broad categories. The simple analgesics, such as aspirin, are most effective against pain of integumentary origin, headache, and muscle-ache; the narcotics are more useful for deep or visceral pain. Narcotic analgesics such as morphine produce more profound effects than simple analgesics, and are potentially addicting, with the development of tolerance and physical dependence. The morphine-like analgesics appear to work through interaction with the endorphin/enkephalin system of the CNS; many, if not all of the simple, non-narcotic analgesics appear to work by inhibition of prostaglandin synthetase. The effect of narcotics is to elevate the pain threshold above the normal level; the non-narcotic analgesics act to raise an abnormally low pain threshold to the normal level. The narcotic analgesics are antagonized by compounds such as naloxone; the non-narcotic analgesics are not.

This invention relates to the discovery that [n]-paradols the pungent and irritating component of Amomum Melequeta Roacoa is a potent analgesic. In this action, it appears to largely unrelated to the two known classes of analgesics. In certain tests, it produces a level of analgesia comparable to morphine, yet it is not antagonized by classical narcotic antagonists such as naloxone. It effectively prevents the development of cutaneous hyperalgesia, but appears to have minimal effects on normal pain responses at moderate dose. At light doses [n]-paradols also exerts analgesic activity in classical deep pain, elevating the pain threshold above the normal value.

BACKGROUND OF THE ART

H. Nomura and S. Tsurumi, Sci. Reports, Tohoku Univ. 16, 565 (1927) state that paradols are known to pungent and irritating components and suggested the synthesizing method of paradols by reacting vanillin and alkylmethyl ketone in the presence of hot alcoholic KOH and then by reducing the obtained compound.

H. D. Locksley and D. K. Rainey, J. Chem. Soc. Perkin I, 23, 3001 (1972) teach the synthesizing method of paradols by reacting vanillin and alkylmethyl ketone in the presence of weak acid and weak base to produce dehydroparadol and then by reducing the compound.

Y. H. Yoon and S. S. Lee, Seoul University Journal of Pharm. Sciences, Vol. 7, 309–317 (1982) state that hydrogenation of dehydroparadol and its long chain homologues can be carried out by rat liver enzyme.

M. Aburada, K. Sugifugi, W. Yuasa and Y. Ikeya, Japanese Laid-open Patent Pub. No. 57-46914 state that the compound of the following formula (I)

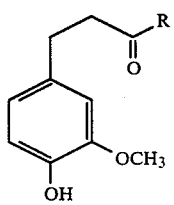

(I)

wherein R is —CH=CH—(CH$_2$)$_4$—CH$_3$ or

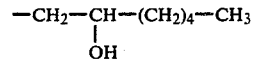

has analgesic property.

DISCLOSURE OF THE INVENTION

This invention provides a method for treating pains in human beings in need of such treatment, comprising administering to the human beings a safe and effective amount of [n]-paradol.

[n]-paradol has the following structure:

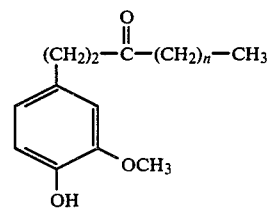

wherein n stands for 6, 7 or 8.

[n]-paradols are easily obtained by reacting vanillin and methyl n-alkyl ketone to produce dehydroparadol and then by reducing the dehydroparadol by use of any methods stated in the background of the art. The reaction scheme is as follows:

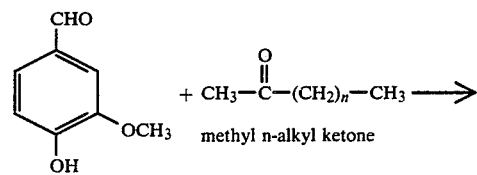

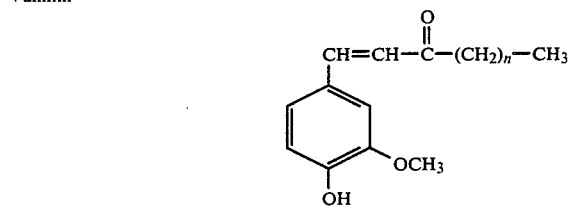

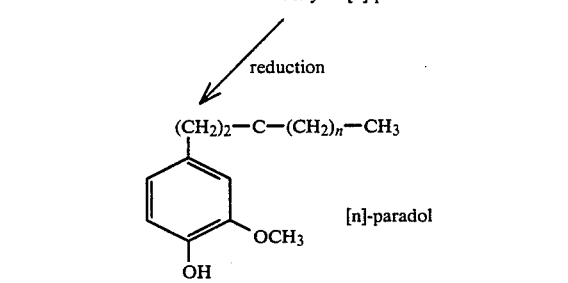

Examples of the [n]-paradols are [6]-paradol [1-(4-hydroxy-3-methoxyphenyl)-3-decanone], [7]-paradol [1-(4-hydroxy-3-methoxyphenyl)-3-undecanone] and [8]-paradol [1-(4-hydroxy-3-methoxyphenyl)-3-dodecanone].

In the practice of this invention, the [n]-paradols can be administered via P. O., I. V. and I. P.

By "safe and effective amount" of [n]-paradol is meant a sufficient amount of [n]-paradols to alleviate or prevent the pain being treated at reasonable benefit/risk ratio attendant judgment, the amount of [n]-paradol used will vary with the particular condition being treated, the severity of the condition, the duration of the treatment, the specific formulation employed and the concentration of [n]-paradols therein, and like factors within the specific knowledge and expertise of the patient or the attending physician.

The broad range of analgesic benefits obtainable by the practice of this invention can be readily appreciated by reference to the following animal experiments.

Phenylquinone Writhing Method

Procedure

This method was designed to detect the analgesic activity based on the frequency of writhing syndrome induced by i.p. injection of phenylquinone (LaHann, 1982). The animals used in this test were male ICR mice weighing from 15 to 25 g. One day prior to test initiation, testing compounds were administered via i.p. injection with sequentially increasing doses of 4, 8, 12, 16 mg/kg at 2 hr interval and via p.o. administration of 50, 100, 150 mg/kg at 4 hr interval. All animals received an i.p. injection of phenylquinone (4.5 mg/kg) and after 10 minutes, the writhing frequency of treated animals was closely observed for 10 minutes.

Result

Analgesic Effects of Paradols: The results obtained from the phenylquinone writhing test of paradols are shown in Table 1. The writhing frequencies of paradols treated mice were significantly lower than those of control. These lower writhing frequencies found in paradols treated mice indicate that they produce anagesic activity. The anagesic activities of paradols were compared with that of control in Table 1. The intensity of anagesic activity was in the order of [7]-paradol, [6]-paradol, and [8]-paradol (Table 1).

Prolonged Anagesic Effects of Paradols: The anagesic durations of paradols are shown in Table 2. Their anagesic effects remained even for 10 days after administration. Paradols-produced anagesia were slightly decreased. (Table 2).

Effects of Paradols on the Mice Growth: The change of mice body weight after administration of anagesia-producing compounds in shown in Table 3. There were no significant differences in the changes of body weight between control and test compound-treated mice. These results indicate that paradols produce no adverse effects which may interfere the growth of mice (Table 3).

TABLE 1

Writhing frequency of administered compounds in the phenylquinone test

| Compounds | i.p. Writhing frequency (WF)[a] | i.p. Inhibition (%)[b] | p.o. Writhing frequency | p.o. Inhibition (%) |
|---|---|---|---|---|
| Control | 58.7 ± 2.2 | 0 | 56.5 ± 2.0 | 0 |
| [6]-Paradol | 23.7 ± 2.5* | 60.0 | 26.8 ± 2.9* | 52.5 |
| [7]-Paradol | 21.0 ± 2.6* | 64.3 | 25.9 ± 3.6* | 54.1 |
| [8]-Paradol | 24.2 ± 2.3* | 58.7 | 28.0 ± 3.5* | 50.4 |

[a]Values are means of experiments ± SE (95% C.L.)

[b] $\frac{\text{WF of control} - \text{WF of compound treated group}}{\text{WF of control}} \times 100$

*p < 0.01 compared with control group.

TABLE 2

Prolonged analgesic effect of paradols in the phenylquinone writhing test.

| Compounds | Post Injection Period (day) 1 | 5 | 10 |
|---|---|---|---|
| Control | 58.7 ± 2.2[a] | 55.0 ± 5.2 | 58.1 ± 6.4 |
| [6]-Paradol | 23.7 ± 2.5* | 24.5 ± 4.5* | 28.7 + 3.0* |
| [7]-Paradol | 21.0 ± 2.6* | 22.5 ± 3.7* | 28.5 ± 2.9* |
| [8]-Paradol | 24.2 ± 2.3* | 25.8 ± 4.4* | 29.4 ± 3.3* |

[a]Table values are means of writhing frequency ± SE.
*p < 0.01 compared with control group.

TABLE 3

| Compounds | Gaining of mice body weight (g) Post Injection Period (day) 0 | 5 | 10 |
|---|---|---|---|
| Control | 19.4 ± 1.2[a] | 25.8 ± 1.9 | 29.6 ± 1.1 |
| [6]-Paradol | 21.4 ± 2.5 | 26.6 ± 3.0 | 30.0 ± 3.1 |
| [7]-Paradol | 20.5 ± 3.1 | 25.1 ± 2.8 | 28.3 ± 3.2 |
| [8]-Paradol | 21.2 ± 1.9 | 26.0 ± 1.8 | 29.1 ± 2.3 |

[a]Mean of body weight ± S.E. (95% C.L.)

Randall-Selitto's Method

Procedure

The paw pressure method described by Randall and Selitto (UGO Basile, Italy) was used to measure the anagesic effectiveness of paradols in rats (Sprague Dawley, male 100-150 g). Inflammation was produced in the right hindpaw of each by injection of 0.1 ml of a 20% suspension of brewer's yeast in saline. One hour later, all rats (six per group) received the test drugs suspended in 2% polysolbate saline via p.o. or i.v. Pain threshold was measured by applying pressure to the inflamed paw at a steadily increasing rate of 16 g/sec and at 1 hr. before administration of drugs and at 0, 30, 60, 120 min. after administration. An analgesic effect was denoted if the individual reaction thresholds were 2 SD or greater than the mean threshold for control group.

Result

Figure 2:
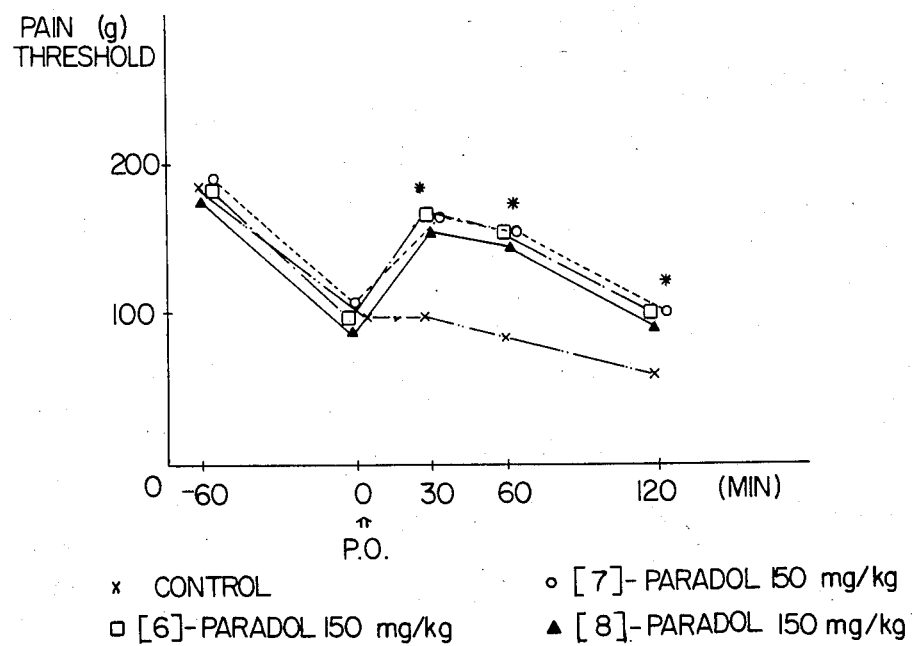

The results with Randall-Selitto's method were shown in FIGS. 1-4. Lowering of the pain threshold value is seen for several hours, when 20% brewer's yeast is administered by hypodermic injection to the right hindpaw. This lowered pain threshold value was restored by administration of paradols (1,4 mg/kg, i.v., and 75, 150 mg/kg, p.o.) respectively.

Paradols were effective inhibitors of brewer's yeast-induced hindpaw edema in rats. When a comparison of paradols' anagesic effects was made, [6]-, [7]- and [8]-paradol were equally potent anti-inflammatory drugs.

What we claim are:

1. A method for treating pain in a human being in need of such treatment, comprising administering to the human being a safe and effective amount of an [n]-paradol, wherein n stands for 6, 7 or 8.

2. A method according to claim 1 is which the [n]-paradol is [6]-paradol.

3. A method according to claim 1 in which the [n]-paradol is [7]-paradol.

4. A method according to claim 1 in which the [n]-paradol is [8]-paradol.

5. A method according to claim 1 in which the [n]-paradols are administered orally.

6. A method according to claim 1 wherein [n]-paradols are administered intravenously.

7. A method according to claim 1 wherein [n]-paradols are administered subcutaneously.

8. A method according to claim 1 wherein [n]-paradols are administered intramuscularly.

* * * * *